United States Patent [19]
Badoz et al.

[11] Patent Number: 5,078,601
[45] Date of Patent: Jan. 7, 1992

[54] DEVICE AND PROCESS FOR DENTISTRY HAND OR ANGLE PIECES

[75] Inventors: Jean-Marie Badoz, Pontarlier; Jacques Pernot, Geneuille, both of France

[73] Assignee: Micro Mega SA, Besancon, France

[21] Appl. No.: 464,408

[22] Filed: Jan. 12, 1990

[30] Foreign Application Priority Data

Jan. 17, 1989 [FR] France .................. 89 00635

[51] Int. Cl.$^5$ ............................................. A61C 1/10
[52] U.S. Cl. ........................................ 433/82; 433/84; 433/114
[58] Field of Search ................... 433/82, 84, 114

[56] References Cited

U.S. PATENT DOCUMENTS

| | | | |
|---|---|---|---|
| 3,256,604 | 6/1966 | Borden | 433/82 |
| 3,952,416 | 4/1976 | Lingenhöle | 433/82 |
| 4,318,695 | 3/1982 | Lieb et al. | 433/82 |

FOREIGN PATENT DOCUMENTS

| | | | |
|---|---|---|---|
| 1907658 | 11/1969 | Fed. Rep. of Germany | 433/82 |
| 23535961 | 5/1974 | Fed. Rep. of Germany | 433/82 |
| 3123390 | 1/1983 | Fed. Rep. of Germany | 433/82 |
| 2482447 | 11/1981 | France | 433/82 |

Primary Examiner—Gene Mancene
Assistant Examiner—Michael Lynch
Attorney, Agent, or Firm—Weiser & Stapler

[57] ABSTRACT

Atomizing process and device for dentistry handpieces or angle pieces, characterized in that it involves generating, in the region of the receptacle of the tool in the handpiece or angle piece, a suction effect putting the vicinity of the cutter receptacle under a slight vacuum under the effect of an air cone of which the apex is situated at the point where the tool is working. the other function of this air cone being to direct the cooling fluid by means of an effect of the COANDA type, thereby reducing the consequences of turbulences attributable to the rotation of the tool or instrument.

16 Claims, 2 Drawing Sheets

DEVICE AND PROCESS FOR DENTISTRY HAND OR ANGLE PIECES

The subject of the present invention is a device equipping the head of a dentistry handpiece or angle piece, the said head being shaped to receive a tool driven in rotation by means accommodated within the said handpiece or the said angle piece and the said head, the head being provided with means for retaining the tool, the said device being of the type having, in the body of the handpiece or angle piece on the one hand and of the head on the other hand, means for the supply and distribution towards the zone to be treated of water and air made to mix with one another to form an atomized mixture, called a "spray", intended for cooling the treated zone and the tool and for evacuating the residues obtained as a result of the work of the tool, the water and air being supplied from longitudinal ducts in the body towards annular chambers in the head, from which they emerge outside by way of a plurality of bores of which the axis is directed towards the tip of the tool.

Devices of this type have been known per se for a long time.

They equip appliances atomizing cooling fluid for dental instruments, such as milling cutters, reamers, etc., equipping dentistry handpieces or angle pieces.

More specifically, the invention relates to an atomizing device incorporated in the head of the handpiece or of the angle piece and producing atomization at several points which are located, for example, under the head of the angle piece and which are distributed round the cutter-shank receptacle.

The invention can be used both on turbine-operated handpieces and on angle pieces in which the instrument is actuated by means of a geared-motor device.

Such an atomizing device is described, for example, in European patent application 0,236,820.

It makes it possible to generate one or more jets of water atomized by the same number of jets of air. This device certainly sprays the rotating tool or instrument efficiently where an instrument rotating at low speed is concerned, but instruments rotating at high speed, including milling cutters mounted on a turbine, generate round them a turbulence tending to repel the cooling fluid away from the cutter which is thus in danger of being sprayed insufficiently and therefore being inadequately cooled.

Other systems exist, such as, for example, that described in the patent DE 3,123,390, or appear in the patent FR 2,206,073. The disadvantage of these devices is that, if the water and air pressures are not set correctly in relation to one another, there is a return of one of the fluids into the conduit or conduits of the other fluid, thereby causing pulsating effects during spraying.

Finally, the disadvantage of all the devices of the prior art is that, when atomization is stopped by the practitioner, a drop of water tends to dwell at the exit of the spraying orifices, the elimination of the said drop requiring either a device called a drop retriever, which is not recommended because the reabsorption of a drop into the fluid pipes causes a pollution of the said pipes incompatible with the effort to reduce risks of cross-contamination, or an air-blowing effect which necessitates stopping the air after the water has been cut off, not every dental apparatus being equipped with this device.

The object of the present invention is to provide an atomizing device for dental handpieces or angle pieces which solve the abovementioned problems and which prevent the risks that polluted particles will penetrate into the head of the angle piece.

The subject of the invention is also a process for preventing such a risk of penetration.

According to the invention, there is provided first of all an atomizing process for dentistry handpieces or angle pieces, characterized in that it involves generating, in the region of the receptacle of the tool in the handpiece or angle piece, a suction effect putting the vicinity of the cutter receptacle under a slight vacuum under the effect of an air cone of which the apex is situated at the point where the tool is working, the other function of this air cone being to direct the cooling fluid by means of an effect of the COANDA type, thereby reducing the consequences of turbulences attributable to the rotation of the tool or instrument.

This process is carried out, according to the invention, by means of a device equipping the head of a dentistry handpiece or angle piece, the said head being shaped to receive a tool driven in rotation by means accommodated within the said handpiece or the said angle piece and the said head, the head being provided with means for retaining the tool, the said device being of the type having, in the body of the handpiece or angle piece on the one hand and of the head on the other hand, means for the supply and distribution towards the zone to be treated of water and air made to mix with one another to form an atomized mixture and to evacuate the residues obtained as a result of the work of the tool, the water and air being supplied from longitudinal ducts in the body towards annular chambers in the head, from which they emerge outside by way of a plurality of bores of which the axis is directed towards the tip of the tool, the said device being characterized in that it delivers an air cone of small thickness under the said head through an orifice of revolution of appropriately oriented axis, and in that in the immediate vicinity of the said air cone, internally or externally in relation to this, water jets are generated around its periphery, each of these water jets being surroundable by an air jet of a cross-section substantially annular at its origin.

The effect of the air jets is to atomize the water, whilst the air cone generates a partial vacuum inside it because it impels the initially static air as a result of gas friction, the consequence of this same effect being, both on the inside and the outside, to guide the atomized water towards the tip of the tool (milling cutter), thereby ensuring a maximum cooling effect.

The invention will be understood better from the following description of non-limiting practical examples, with reference to the accompanying drawings in which.

It will be recalled, first of all, that, according to the general process of the invention, a suction effect is generated in the region of the receptacle of the tool in the handpiece or angle piece and puts the vicinity of the cutter receptacle under a slight vacuum under the effect of an air cone of which the apex is situated at the point where the tool is working.

Associated with this structure is a plurality of water jets arranged on the periphery of the said cone internally or externally, the said jets being of any number.

Advantageously, still according to the same process, each water jet will be surrounded by an air cylinder intended to produce atomization.

Figure 1:
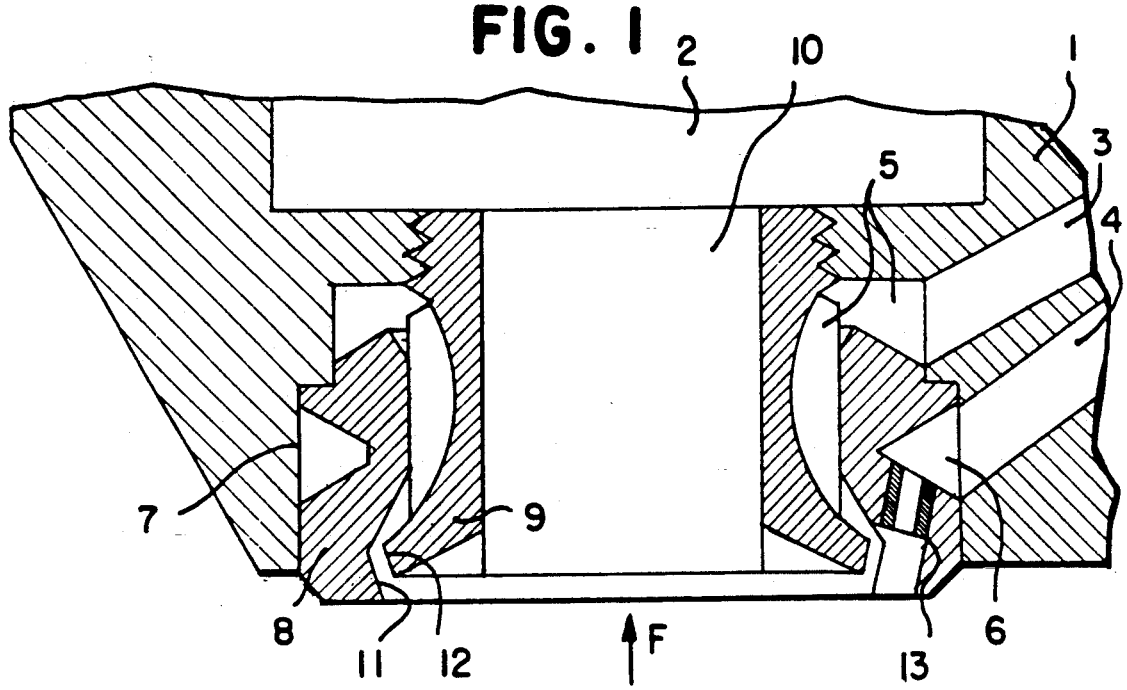
FIG. 1 is a sectional view of a device according to the invention.
Figure 2:
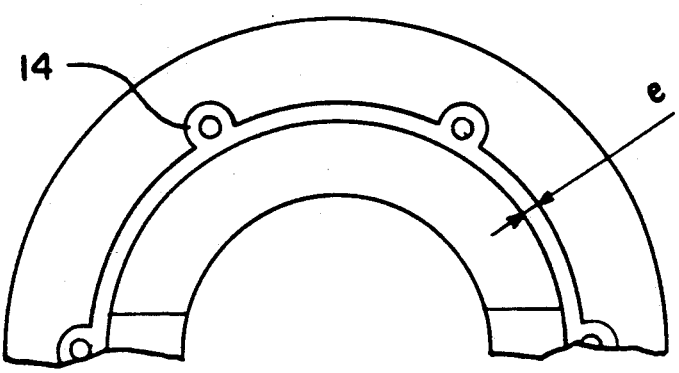
FIG. 2 is a half-view according to F of FIG. 1.

FIGS. 1 and 2 illustrate an embodiment of the invention, in which an angle-piece head (1) can receive, in a receptacle (2), either an air-turbine device or a geared angle piece device (not shown). The angle-piece head (1) is provided with two ducts for fluids, air (3) and water (4) respectively, produced in a known way and opening respectively into hollow volumes of revolution (5) and (6) obtained by installing in the bore (7) of the head (1) a ring (8), mounted sealingly in the head (1) by known means, and a bush (9) entering (8) and forming in its axis a bore (10) for the passage of the shank of a rotary instrument (not shown). The ring (8) has a female cone (11) associated with and concentric with a male cone (12) and (9), in such a way that the air under pressure coming from (3) is projected outside the head, at the same time forming a hollow air cone of a wall thickness (e) at its origin.

The ring (8) receives bushes (13) functioning as water nozzles, distributed round the base of the air cone and oriented in such a way that the water jet is sufficiently near to the cone to benefit from the COANDA effect. Furthermore, the jet emerges into a bore (14) which can intersect the cone (11), the effect of this being to produce an air cylinder continuous with the air cone, reinforcing both the atomizing effect and the effect of protecting the water jet from the turbulences generated by a rotating cutter shank.

Figure 3:
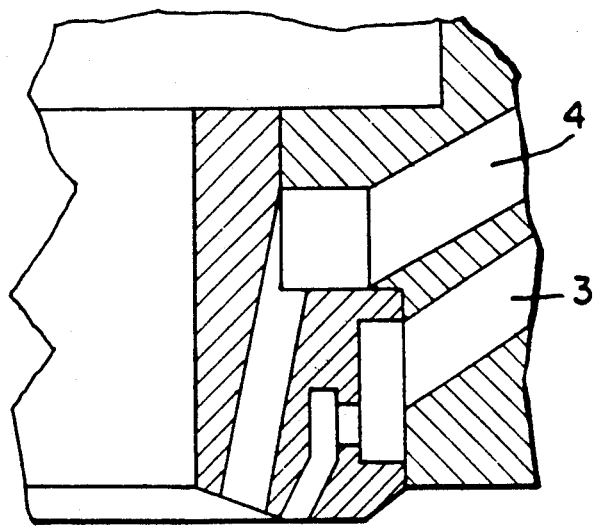
FIG. 3 is a sectional half-view of a device according to the invention, in an embodiment in which the jets are on the inside of the air cone.

FIG. 3 shows a simplified structure, in which the water jets developed by the air (3) and water (4) ducts are not surrounded by air cylinders, the water jets thus necessarily being internal to the air cone.

Figure 4:
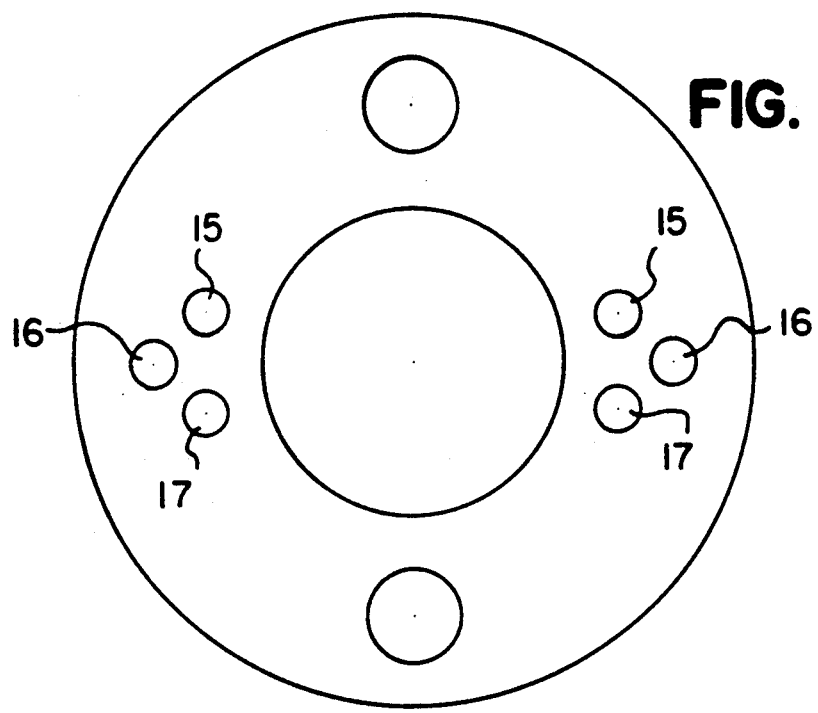
FIG. 4 is a partial diagrammatic plan view of an alternative version.
Figure 4A:
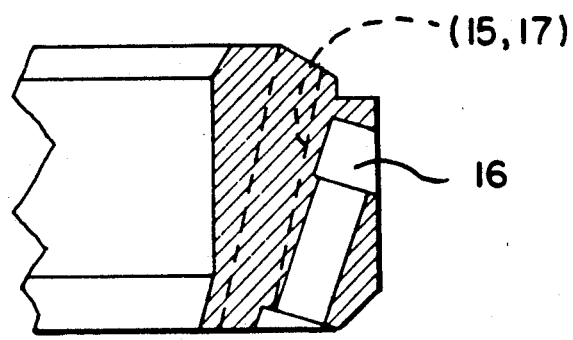
FIG. 4A is a partial section through the alternative version of FIG. 4.

In the alternative version of FIG. 4, the same result is obtained by replacing the air cone and the water outlets with groups of three outlets (15, 16, 17) arranged in the form of a triangle and comprising two outlets (15, 17) for the air surrounding one outlets (16) for the water. There can, for example, be two groups diametrically opposite one another.

What is claimed is:

1. A process for atomizing a mixture of air and water in a dentistry handpiece or anglepiece having a head including an axial receptacle for receiving a tool for use with the handpiece or anglepiece, comprising the steps of:
    producing jets of air and water issuing from the head in a region adjacent to the receptacle form the tool, placing the region adjacent to the receptacle under a slight vacuum and developing a suction effect in said region;
    forming a cone of air having an apex located adjacent to tip portions of the tool so that cooling fluid is directed toward the tool, and so that turbulance attributable to rotation of the tool is reduced.

2. The process of claim 1 which further includes forming the periphery of said cone by issuing a plurality of water jet from the head.

3. The process of claim 2 wherein the water jets are located externally of the air jet.

4. The process of claim 2 wherein the water jets are located internally of the air jet.

5. The process of claim 1 which further comprises the step of forming an air cylinder for entraining the water jet, atomizing the air and water jets.

6. A dentistry handpiece or anglepiece having a head for receiving a tool adapted for rotation by means accommodated within the handpiece or anglepiece and the head, wherein the head includes means for directing an atomized mixture of water and air toward a region to be cooled with the atomized mixture, for cooling the region and the tool, and for evacuating residues resulting from operations of the tool, including means for producing a cone-shaped jet of air issuing from the head for entrained jets of water extending about the periphery of the cone-shaped air jet, wherein the water and air are supplied from longitudinal ducts communicating with annular chambers formed in the head so that the atomized mixture of water and air emerges from a plurality of bores directed toward tip portions of the tool.

7. The apparatus of claim 6 wherein the cone-shaped air jet constitutes a thin cone of air issuing from the head.

8. The apparatus of claim 6 wherein the cone-shaped air jet issues from an orifice formed in the head.

9. The apparatus of claim 6 wherein the jets of water and air surround one another.

10. The apparatus of claim 9 wherein the water jet is located externally of the air jet.

11. The apparatus of claim 9 wherein the water jet is located internally of the air jet.

12. The apparatus of claim 6 wherein the head includes an air duct and a water duct opening into hollow volumes of revolution formed in the head.

13. The apparatus of claim 12 wherein the head includes a ring sealingly mounted in the head, and a bush entering and forming an axial bore for receiving the shank of a rotary instrument, the ring having a female cone concentric with a male cone so that air issuing under pressure is projected outside of the head while at the same time forming a hollow cone of air.

14. The apparatus of claim 13 wherein the ring receives a plurality of bushes functioning as water nozzles, distributing around the base of the cone of air and oriented so that the water nozzles are sufficiently near to the cone of air to entrain the water jet by suction effect.

15. The apparatus of claim 6 which further comprises groups of three outlets each, arranged in the form of a triangle and including two air outlets surrounding one water outlet.

16. The apparatus of claim 15 which includes two groups of outlets diametrically opposite one another.

* * * * *